US012638600B2

(12) United States Patent
Sundal

(10) Patent No.: US 12,638,600 B2
(45) Date of Patent: May 26, 2026

(54) SENSOR

(71) Applicant: Airthings ASA, Oslo (NO)

(72) Inventor: Bjørn Magne Sundal, Oslo (NO)

(73) Assignee: Airthings ASA, Oslo (NO)

( * ) Notice: Subject to any disclaimer, the term of this patent is extended or adjusted under 35 U.S.C. 154(b) by 510 days.

(21) Appl. No.: 18/027,361

(22) PCT Filed: Sep. 21, 2021

(86) PCT No.: PCT/EP2021/075947
§ 371 (c)(1),
(2) Date: Mar. 20, 2023

(87) PCT Pub. No.: WO2022/063779
PCT Pub. Date: Mar. 31, 2022

(65) Prior Publication Data
US 2023/0375724 A1 Nov. 23, 2023

(30) Foreign Application Priority Data

Sep. 22, 2020 (GB) ...................................... 2014966

(51) Int. Cl.
| | |
|---|---|
| *G01T 1/178* | (2006.01) |
| *G01N 33/00* | (2006.01) |
| *H05K 1/183* | (2026.01) |

(52) U.S. Cl.
CPC ......... *G01T 1/178* (2013.01); *G01N 33/0055* (2013.01); *H05K 1/183* (2013.01);
(Continued)

(58) Field of Classification Search
CPC .... G01T 1/178; G01N 33/0055; H05K 1/183; H05K 2201/10106; H05K 2201/10545
See application file for complete search history.

(56) References Cited

U.S. PATENT DOCUMENTS

| | | | |
|---|---|---|---|
| 4,871,914 A | 10/1989 | Simon et al. | |
| 5,489,780 A | * 2/1996 | Diamondis | ............ G01N 23/00 250/DIG. 2 |

(Continued)

FOREIGN PATENT DOCUMENTS

| | | | |
|---|---|---|---|
| EP | 1696404 A1 * | 8/2006 | ............. G09F 13/22 |
| GB | 2 328 014 A | 2/1999 | |

OTHER PUBLICATIONS

International Search Report and Written Opinion for PCT/EP2021/075947, mailed Jan. 4, 2022, 58 pages.

(Continued)

*Primary Examiner* — Uzma Alam
*Assistant Examiner* — Fani Polyzos Boosalis
(74) *Attorney, Agent, or Firm* — Klarquist Sparkman, LLP

(57) ABSTRACT

A sensor comprising: a printed circuit board; a photosensor mounted on a first side of the printed circuit board; and a light source mounted on a second, opposite side; wherein the light source is arranged to transmit light through at least a portion of the printed circuit board, which is impermeable to air. Positioning of the light source on the opposite side of the printed circuit board from the photosensor means that the bulk of the printed circuit board lies between the light source and the photosensor, obstructing direct transmission of light from the light source to the photosensor. However, light can be transmitted through the printed circuit board itself without drilling a hole through the printed circuit board. In this way, the light source can be mounted on the opposite side of the printed circuit board from the photosensor while still transmitting light to the photosensor.

18 Claims, 3 Drawing Sheets

(52) U.S. Cl.
      CPC .............. *H05K 2201/10106* (2013.01); *H05K*
                                    *2201/10545* (2013.01)

(56)                          References Cited

U.S. PATENT DOCUMENTS

| | | | | |
|---|---|---|---|---|
| 10,834,825 | B1 * | 11/2020 | Bedinger | ............. H05K 3/4038 |
| 11,275,183 | B2 * | 3/2022 | Gordon | ................... G01T 1/185 |
| 12,282,007 | B2 * | 4/2025 | Waltl | ................. G01N 33/0055 |
| 2009/0230305 | A1 | 9/2009 | Burke et al. | |
| 2019/0072676 | A1 | 3/2019 | Loi et al. | |

OTHER PUBLICATIONS

IPO Search Report under Section 17(5) for GB2014966.2, dated
Mar. 15, 2021, 3 pages.

* cited by examiner

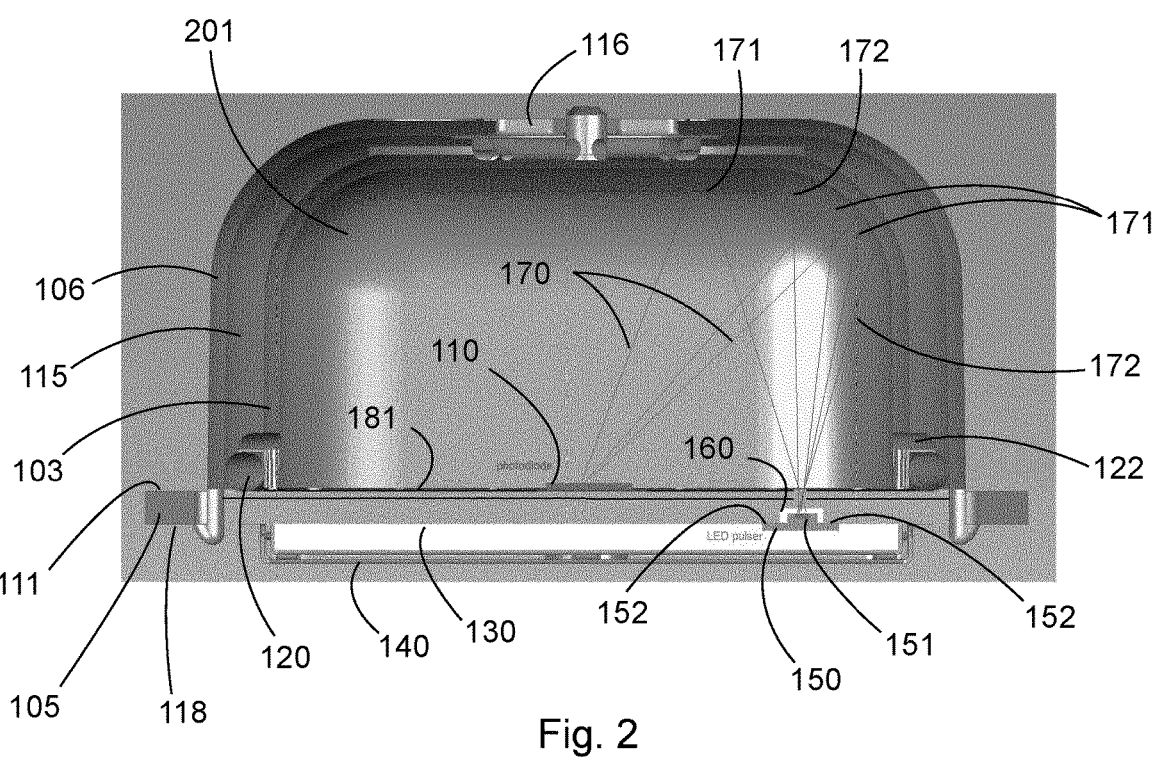
Fig. 2
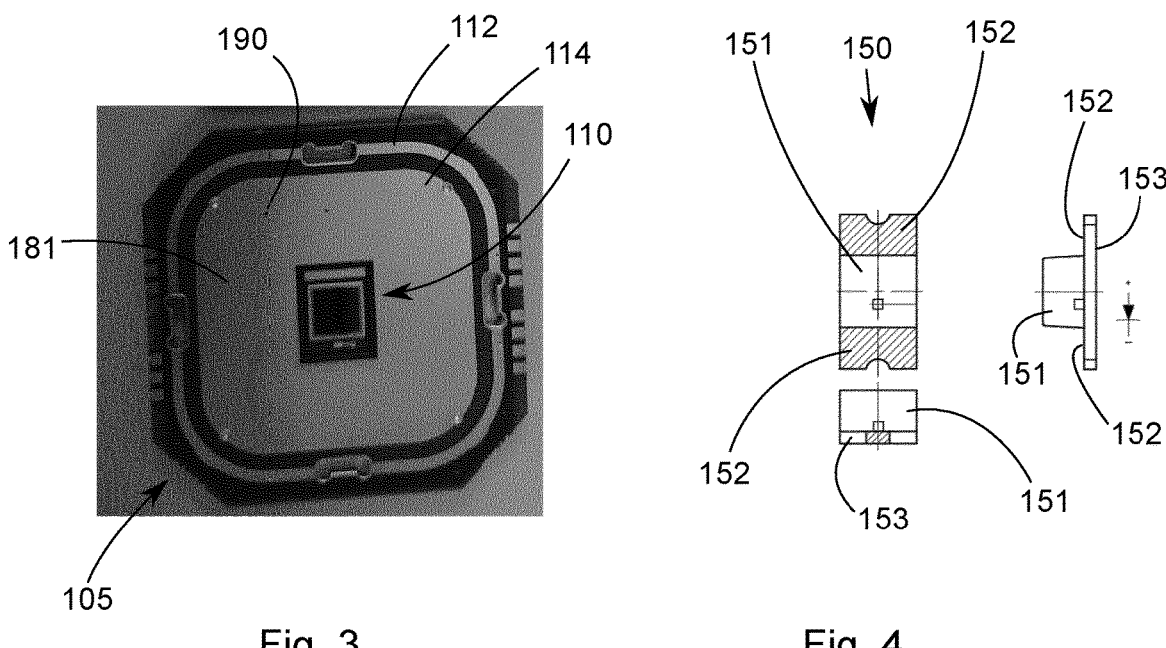
Fig. 3                              Fig. 4

SENSOR

CROSS REFERENCE TO RELATED APPLICATIONS

This is the U.S. National Stage of International Application No. PCT/EP2021/075947, filed Sep. 21, 2021, which was published in English under PCT Article 21(2), which in turn claims the benefit of Great Britain Application No. 2014966.2, filed Sep. 22, 2020.

The present invention relates to sensors, in particular to photosensors and more particularly to radon gas sensors.

Radon is a radioactive element which at normal temperature and pressure is a gas. It is colourless, odourless and tasteless which means that its presence and concentration is not readily detectable by human beings. However, due to its radioactivity, it can be harmful if the concentration is too high. At normal concentrations, radiation from radon typically accounts for around half of a person's annual natural radiation dose.

The most stable isotope of radon is radon-222 which has a half life of 3.8 days and is produced as part of the decay chain of uranium-238 which is present throughout the Earth's crust. Being a noble gas, radon readily diffuses out of the ground and into the air around us. The daughter products of radon decay tend to be charged particles which will readily stick to dust or smoke particles in the air. When these particles are inhaled, they can lodge in the lungs and the subsequent radiation from decay of the radon daughter products causes a risk of lung cancer. Consequently, higher concentrations of radon lead to higher risks of cancer.

The concentration of radon in the atmosphere depends, amongst other things, on ventilation. Areas with good ventilation will have lower radon concentrations, whereas a lack of ventilation leads to radon accumulation and thus increases the radiation level in such areas. Radon levels outside therefore tend to be lower than inside buildings. For example, typical radiation doses from radon may be around 10-20 Bq/m$^3$ outside and may be around 100 Bq/m$^3$ inside. Radon levels can also vary significantly due to variations in geographic location (e.g. different geologies), or due to differences in building materials.

Radon decays by emission of an alpha particle with an energy of 5.5 MeV. The resultant Polonium-218 has a half life of about 3 minutes before emitting an alpha particle of 6.0 MeV. The resultant Lead-214 has a half life of around 27 minutes before beta-decaying to Bismuth-214 which in turn has a half life of 20 minutes and beta-decays to Polonium-214. Polonium-214 has a half life of about 164 microseconds before emitting an alpha particle of 7.7 MeV resulting in Lead-210 which has a half life of 22 years and is thus relatively stable.

Detection of radon to date has been divided into two main methods. The first method is active detection of alpha particles using a photodiode and the second method is passive detection of alpha particles using a track detector. Typically the first method requires a large instrument and needs electrical power to be supplied. Such instruments have typically only been used for larger scale, e.g. commercial or industrial measurements as the instruments are more bulky and expensive. The photodiode (e.g. a PIN diode) is placed in a diffusion chamber of the device. Alpha particles hitting the photodiode create a number of electron-hole pairs which will cause a small current to be generated. These current signals can be detected and counted to provide a measure of the radon concentration within the diffusion chamber. Such active measurements can be provided continuously in time rather than having to wait for the results of a laboratory analysis.

The second method uses much smaller detectors with no power requirement and is thus much more suited to domestic customers. A passive (i.e. unpowered) track chamber is typically placed in a selected location and left for a predetermined period of time (typically from a few weeks and up to about 3 months) after which it is sent back to a lab for analysis. Alpha particles emitted within the chamber leave tracks on a film which is also disposed within the chamber. These tracks can be detected in the lab and counted thus providing a measure of the radon concentration in the air within the chamber.

US 2009/0230305 describes an active radon detector device which is battery powered. The photodiode detector is mounted on the main PCB and is covered by a sampling chamber, also mounted on the main PCB. Air enters and leaves the sampling chamber through apertures in the PCB. These apertures are optionally covered by a filter to exclude undesired debris such as smoke, dust, and the like.

U.S. Pat. No. 5,489,780 describes another active radon detector device in which a pressed metal filter is used as the wall of the diffusion chamber. This filter is mounted directly on the PCB over the photodiode detector, thus defining the sampling volume.

Another known type of active radon detector is a Lucas cell. A Lucas cell is a chamber in which a gas sample is collected, the inside of the chamber being coated with a scintillating material such as Silver-doped Zinc Sulphide. This scintillating material emits light when struck by alpha particles. A photomultiplier tube is arranged to view the inside of the chamber (e.g. through a window) and counts the light flashes caused by the scintillation, thereby counting the number of alpha particle disintegrations.

In all of these active sensors, the sensor is a photosensitive sensor, i.e. it outputs a signal when light is incident upon the sensor surface, typically visible light. In the case of the silicon photomultiplier, the sensor detects radon particles through detection of photons of visible light. In the case of a photodiode (e.g. PIN diode), while the sensor reacts to an incident alpha particle, it is also sensitive to incident photons of visible light and produces a signal when such photons are incident on the sensor surface.

It is desirable to be able to verify that the photosensor is functioning correctly so as to provide diagnostics and to aid in error detection and/or calibration. One way to do this is to have a light source that can be controlled to produce light on demand so that the signal from the photosensor can be evaluated to verify that that light was indeed detected (and optionally the properties (e.g. strength) of the received signal compared with the properties of the transmitted light. The use of a light source to detect the correct functioning of a photosensor in this general manner is known.

Photosensors are normally used in a particular light environment so that variations in the light levels within that environment can be detected. For example, in the case of radon sensors, the sensor is located within a diffusion chamber that is sealed to light. In such sensors, ideally no stray light can enter the diffusion chamber so that signals from the photosensor can be guaranteed to originate from an event (e.g. an alpha particle disintegration) within the diffusion chamber. It is therefore important that the light source for testing the photosensor is arranged to generate light within that light environment (e.g. within the diffusion chamber of a radon sensor).

It will be appreciated that while the above background has been set out predominantly in the context of radon sensors, the arrangements described herein are more broadly applicable and may be applied to other devices that make use of photosensors is part of a detection process.

According to one aspect of the invention, there is provided a sensor comprising:

a printed circuit board;

a photosensor mounted on a first side of the printed circuit board; and a light source mounted on a second, opposite side of the printed circuit board;

wherein the light source is arranged to transmit light through at least a portion of the printed circuit board, said portion being impermeable to air.

Positioning of the light source on the opposite side of the printed circuit board from the photosensor means that the bulk of the printed circuit board lies between the light source and the photosensor, obstructing direct transmission of light from the light source to the photosensor. This is therefore not an ideal location for the light source from a practical perspective. However, mounting the light source to the printed circuit board on the same side as the photosensor also adds complications. A first complication is that the mounting of the photosensor to the printed circuit board is a special assembly step involving wire bonding that is normally done in a clean room and would need to be done after mounting the light source. The light source would typically be a packaged product requiring soldering to the printed circuit board. However, residues from the soldering process for mounting the light source can interfere with the wire bonding process. Wire bonding the light source is unattractive from a cost perspective. A second complication is simply that mounting (e.g. using surface mount technology) components to both sides of the printed circuit board is a more expensive process than only mounting them to a single side. It is desirable to mount the signal processing circuitry separate from the photosensor so that the sensor can be electromagnetically isolated for improved sensitivity. Thirdly, mounting the light source (and providing its electrical connections) on the same side as the photosensor can interfere with the electric field that may be set up around the photosensor (as is the case for example in a radon sensor). It is therefore preferred to mount the light source to the second side of the printed circuit board on the same side as other processing circuitry.

There are reverse mount light source devices (e.g. LEDs) available for mounting to a printed circuit board (e.g. using surface mount technology) so that the light shines into the printed circuit board rather than away from it. Such devices are useful for example to increase flexibility in the location of status lights in a product (e.g. they can be provided on the same surface to which the PCB is mounted. Such devices are typically "gullwing" devices with the electrical contacts provided on the same side as the light source. They are mounted by drilling a hole through the printed circuit board into which the light source can be placed, with the electrical contacts mounted (and being soldered) either side of the hole. However, such an arrangement is incompatible with certain sensors as the hole that is drilled to allow light to shine through the printed circuit board also allows air to pass through. While the hole could be sealed, e.g. with a resin glob top, this is a messy process with the potential for leakage through the hole which can block the light or even leak onto the other side of the PCB. As an example, radon sensors require a highly controlled volume of air around the sensor. The sensor is placed in a diffusion chamber into which air can enter only by way of a diffusion path with characteristics that ensure the radon daughter products do not enter the diffusion chamber. In this way, any detected alpha particle disintegrations within the chamber are safely assumed to originate from a radon atom within the diffusion chamber. It will be appreciated that a through hole as is used for reverse mount LEDs would provide an alternative path for air into the diffusion chamber and is therefore not a possibility. However, the invention recognises that light can be transmitted through the printed circuit board itself without drilling a hole through the printed circuit board. In this way, the light source can be mounted on the opposite side of the printed circuit board from the photosensor while still transmitting light that can reach the photosensor and also not providing an air path across the printed circuit board.

While the light source could be any type and shape of light source and could be mounted in a suitable frame for directing its light into the printed circuit board, it is advantageous to make use of available technology and to avoid additional support structures or assembly processes. Reverse mount components such as reverse mount LEDs typically have a base plate with electrical contacts and a light source projecting from the base plate on the same side as the electrical contacts. Therefore the projecting light source needs a recess in the printed circuit board into which the light source can be placed so as to bring the electrical contacts adjacent to the printed circuit board. In normal use, this recess is provided by the through hole drilled through the printed circuit board. However, in preferred embodiments of the invention a blind hole is formed in the second side of the printed circuit board and the light source is arranged to transmit light into the blind hole. The blind hole is not a through-hole, i.e. it does not extend all the way through the printed circuit board, but instead extends only part way through the printed circuit board. Blind holes require more care and precision in manufacturing, particularly with thin structures such as printed circuit boards, to ensure that the hole does not go all the way through the printed circuit board. The blind hole ensures that air flow is blocked while the light source can still be recessed into the printed circuit board. In addition, as there is less material of the printed circuit board for the light to pass through, more light from the light source can reach the photosensor. This is also important as the material of the printed circuit board is translucent, but will still absorb some of the transmitted light. Therefore reducing the thickness of this material will reduce the light absorption.

The depth of the blind hole needs to be deep enough to accommodate the particular light source being used, but as noted above also advantageously reduces the material thickness of the printed circuit board and therefore may in some examples be deeper than is necessary to accommodate the light source. In some embodiments the blind hole has a depth equal to at least a quarter the thickness of the printed circuit board, preferably at least a third the thickness of the printed circuit board, preferably at least half the thickness of the printed circuit board. Printed circuit boards come in different thicknesses, but common thickness include around 0.8 mm, 1.6 mm and 2.4 mm with 1.6 mm being the most common. In some examples the blind hole may have a depth equal to at least 0.3 mm, at least 0.5 mm or at least 0.8 mm.

Another consideration is that printed circuit boards can be manufactured with multiple layers. The simplest construction has a single conductive layer on one side of the printed circuit board. Double sided printed circuit boards have a conductive layer on both sides. Further layers can be included inside the printed circuit board for ease of routing and for creating ground or power planes. Such internal layers are usually created by starting with a conductive layer on one side of a printed circuit board, appropriately etching or shaping that layer, then applying an insulating prepreg layer over the top with a further conductive layer on top of that which can be further etched or shaped. As an example, in a typical four layer board, the prepreg laminate is typically a lot thinner than the main core of the printed circuit board. Therefore with a core thickness of around 1.2 mm and a prepreg laminate thickness of about 0.2 mm, a total printed circuit board thickness of 1.6 mm is obtained, but with the two conductive layers on each side being separated only by 0.2 mm. It will be appreciated that the thickness of the core and the prepreg can vary with application, as can the number of layers. However, a consideration in the forming of the blind hole is that it can cut through a number of these layers, thereby avoiding the requirement to etch those layers to allow light transmission. Therefore a deeper blind hole can cut through more intermediate layers. In some preferred examples, the blind hole passes through at least two conductive layers (one surface layer and one internal layer).

As discussed above, the light source may be at least partially located within the blind hole. As well as being space efficient and convenient for the typical shape of reverse mount light sources, this also brings the light source closer to the output surface (the first side of the printed circuit board).

The printed circuit board may comprise a substrate layer of translucent electrically insulating material. In some examples this may be a fibre-reinforced polymer material. The most common materials used in printed circuit boards are designated "FR4" and are translucent such that the light from the light source can be transmitted through the FR4 material to reach the photosensor. It will be appreciated that other electrically insulating, translucent materials may be used.

In the case of multilayer printed circuit boards, it will be appreciated that each conductive layer will block light transmission, i.e. it is opaque to light. Therefore in order for light from the light source to reach the photosensor, all intervening conductive layers must be appropriately removed from the light path. Such removal may be by any suitable process, but in some examples may be a material removal process such as etching. In other examples the conductive layer may be deposited by a deposition process with an appropriate area left clear for light transmission. Therefore in some embodiments the first side of the printed circuit board comprises a first opaque conductive layer on the surface of the first side opposite the light source and wherein the first opaque conductive layer comprises a hole to allow light from the light source to pass through. It will be appreciated that while the opaque conductive layer has been removed (or not deposited), the underlying substrate is still left intact so as to block airflow through the light path. It will be appreciated that other regions of the opaque conductive layer may also be shaped for other purposes such as to form conductive traces as part of the circuit. However, in some embodiments the first opaque conductive layer may substantially cover the area of the first side of the printed circuit board in which the hole is formed. For example the hole may be formed in a continuous area of the first opaque conductive layer (e.g. an area of at least 10 square millimetres, or at least 20 square millimetres, at least 50 square millimetres or at least 100 square millimetres). In some examples the first opaque conductive layer may form part of a constant voltage surface which can be held at a potential relative to the photosensor so as to create an electric field therebetween. Such arrangements are used for example in Radon sensors in which an electric field helps to draw charged Radon daughters to the photosensor. In such cases it is desirable for the first opaque conductive layer to be as continuous is possible so as to create as homogenous as possible an electric field.

In some examples the hole in the first opaque conductive layer is no more than 5 mm wide in any dimension, preferably no more than 3 mm wide in any dimension, preferably no more than 2 mm wide in any dimension, preferably no more than 1 mm wide in any dimension.

The same principles as above also apply to intermediate layers of the printed circuit board which might otherwise block the light path. Therefore in some examples the printed circuit board further comprises a second opaque conductive layer located within the printed circuit board and wherein the second opaque conductive layer comprises a hole to allow light from the light source to pass through. The same principles as above regarding material removal or deposition and area also apply to this second opaque conductive layer, although it will be appreciated that for any layer sufficiently far from the first side of the printed circuit board, the material may be removed by a material removal process that removes both the internal conductive layer and the insulating substrate material (e.g. to form the aforementioned blind hole by drilling or milling or the like).

The hole in the second opaque conductive layer may be no more than 5 mm wide in any dimension, preferably no more than 3 mm wide in any dimension, preferably no more than 2 mm wide in any dimension, preferably no more than 1 mm wide in any dimension.

As discussed above, in some embodiments the first opaque conductive layer and the second opaque conductive layer are separated by a layer of translucent electrically insulating material. This layer could be the prepreg layer discussed above. It may be formed from the same or similar material to the main substrate (i.e. an FR4 material), although it may be softer and more pliable (in sheet form). In some examples it may be a fibreglass impregnated with resin where the resin is uncured (although it may be hardened to some degree).

The light source may be any suitable light source that generates light of an appropriate wavelength for detection by the photosensors. Light sources that generate visible light are normally suitable, especially for the photodiodes or photomultipliers used in radon detectors. The light source is preferably a semiconductor light source that can be switched on and off very fast so that it can generate a highly controllable amount of light. By generating light pulses of known intensity and/or duration, the amount of light received at the sensor can be controlled to simulate certain events. For example, in a radon sensor, the light sensor may be controlled to generate light pulses that simulate the detection of alpha particles of different energies. This allows not only the functionality of the photosensor to be verified, but also the functionality of the processing circuitry. The light source may therefore be used in fault detection and/or calibration of the sensor.

As discussed above, the light source may be a reverse assembly surface mount light source.

The light source may be a semiconductor laser. However, in preferred embodiments the light source is a light emitting diode. Light emitting diodes are inexpensive and readily available in small form factors, and in particular in reverse mount form factors that can readily be used in consumer electronics.

The light source may be arranged to block light through the printed circuit board that does not originate from the light source. Any stray light passing through the printed circuit board may reach the photosensor and disturb the sensor readings leading to inaccuracies in the sensor. For example, the light source may be arranged to fit snugly in or against the entrance to the light path through the printed circuit board so that no light can pass through the printed circuit board from other sources. However, such arrangements require high precision in the definition of the light path (e.g. high precision milling of the blind hole in the printed circuit board) and/or high precision in the mounting of the light source, e.g. to ensure that no gaps exist between the light source component and the printed circuit board that could allow stray light through. However, in practice such precision is difficult and expensive. An opaque resin glob top is also not attractive as discussed above as the resin may inadvertently cover or partially cover the light source, thereby altering or entirely blocking the generated light from reaching the sensor. Therefore in preferred examples the light source is located within an opaque enclosure mounted on the second side of the printed circuit board. The opaque enclosure can surround the light source either by itself or can also surround other processing circuitry. The opaque enclosure may be a Faraday cage that is in electrical contact with the printed circuit board and provides electromagnetic shielding to the components within the opaque enclosure. This is particularly advantageous when the opaque enclosure also surrounds the processing circuitry as such circuitry can often be highly sensitive to noise due to the low signal levels deriving from the photosensor. The opaque enclosure may therefore be formed from a conductive material, e.g. metal.

The arrangements described here may apply to a number of different sensors, but they are particularly applicable to sensors that have an enclosed or controlled volume in which the photosensor is located. Therefore in some embodiments the sensor comprises an opaque chamber mounted on the first side of the printed circuit board over the photosensor and wherein the light source is arranged such that the light transmitted through the printed circuit board is transmitted into the inside of the opaque chamber. It will be appreciated that this opaque chamber is opaque in the sense of being impervious to transmission of light from inside the chamber to outside the chamber and vice versa, but it may be reflective as discussed below.

In some embodiments the sensor is a radon gas sensor and the opaque chamber is a diffusion chamber. The diffusion chamber is a controlled air space in which the passage of air into and out of the chamber is only possible along a diffusion path with carefully chosen dimensions to ensure certain characteristics of the air within the chamber, e.g. that substantially no radon daughter products (such as Polonium-214 and Polonium-218) enter the diffusion chamber. The inside surface of the opaque chamber may be reflective so as to bounce the light from the light source back towards the photosensor.

An inside surface of the opaque chamber may be at least partially covered with a scintillating material. This may for example be the case for a sensor using a photomultiplier as the photosensor. In addition to emitting light in response to radiation impact, the scintillating material may be reflective so as to reflect light from the light source towards the photosensor. One example of a suitable reflective scintillating material is Silver-doped Zinc Sulphide.

Most surfaces will scatter incident light to some degree. Therefore light emitted by the light source will hit the inside surface of the opaque chamber and be scattered in all directions such that some of that light (and indeed a predictable quantity of it) will hit the photosensor. However, the quantity of light that reaches the photosensor is influenced by the angle at which the light hits the surface. For example more highly reflective surfaces will reflect more light in a particular direction (determined by the angle of incidence of the light) while scattering less light in other directions. Therefore the amount of light reaching the photosensor can be increased by suitably selecting the geometry of the incident light, the opaque chamber's interior surface and the photosensor. For example, the directions of light entering the opaque chamber from the light source may be determined by the position of the light source and the position of opaque material on the surface of the printed circuit board (e.g. conductive layers). In some examples described above, light passes through a hole in a conductive layer on a first side of the printed circuit board. The size and location of this hole together with the relative location of the light source (typically aligned with that hole but mounted on the opposite side of the printed circuit board) determine the angles at which light can enter the opaque chamber. This light will form a cone of light exiting from the hole and directed away from the printed circuit board towards the interior surface of the opaque chamber. The angle of the opaque chamber at the positions where the incident light hits it determines the dominant direction of reflected light.

The opaque chamber may be shaped in a number of different ways and will to some extent be determined by the desired sensor characteristics. However, that shape may either be selected, or may be used to increase the amount of light from the light source that is reflected onto the photosensor. For example if the opaque chamber has a substantially planar roof portion parallel to the printed circuit board, the position of the hole that permits light to enter the chamber from the light source may be chosen so that light from the light source is directed at that roof portion at an angle that will reflect back to the photosensor. However, such a geometry may require a significant angling of the light from the light source relative to the normal to the printed circuit board. It is easier to direct the light from the light source at a normal to the surface of the printed circuit board as a hole in the printed circuit board is most easily drilled or milled normal to the surface. Instead, if the opaque chamber has a curved portion of its interior surface then the light source can be positioned (and directed normal to the surface of the printed circuit board) such that the cone of light from the light source is incident on the curved portion. The effect of the curved portion is to reflect the light from the light source across a range of angles, some of which will hit the photosensor. In the case of a singly-curved surface (i.e. one that can be formed by bending a plane), this spreading effect will occur in one dimension such that the light source must still be aligned with the photosensor in the other (perpendicular) dimension. However, in some embodiments the inside surface of the opaque chamber has a doubly-curved region and the light source is arranged to transmit light towards the doubly-curved region. The doubly-curved region (which may also be referred to as a developable surface or one with non-zero Gaussian curvature) will spread the light from the light source over a wider area, thereby allowing the light source to be positioned remotely from the photodiode, e.g. in the corner of the opaque chamber. This can be a big advantage in cases where an electric field is used within the opaque chamber (such as in the diffusion chamber of a radon sensor) as the opening above the light source can be far away from the photosensor where it provides less distortion to the electric field. The field strength is much higher and important near the photo-sensor than it is in the outer regions of the diffusion chamber close to the wall/floor. It is desired that the field strength close to the photosensor be as good as possible at directing ions towards the photosensor surface.

Any type of photosensor may benefit from the arrangements described above, but in some examples the photosensor comprises a photodiode and/or a semiconductor photomultiplier. Such sensors are used for (amongst others) Radon sensors. The photodiode may be a PIN diode. The semiconductor photomultiplier may be a Silicon photomultiplier.

According to another aspect of the invention, there is provided a method of testing a photosensor mounted on a first side of a printed circuit board, comprising:

transmitting light from a light source mounted on a second side of the printed circuit board through at least a portion of the printed circuit board, said portion being impermeable to air; and receiving said light at said photosensor.

It will be appreciated that all of the preferred and optional features described above in relation to the sensor apply equally and correspondingly to the method of testing the photosensor.

Preferred embodiments of the invention will now be described, by way of example only, and with reference to the accompanying drawings in which:

FIG. 2 shows the arrangement of a light source and photosensor;

FIG. 3 shows the printed circuit board;

FIG. 4 shows a surface mount light emitting diode; and

Figure 1:
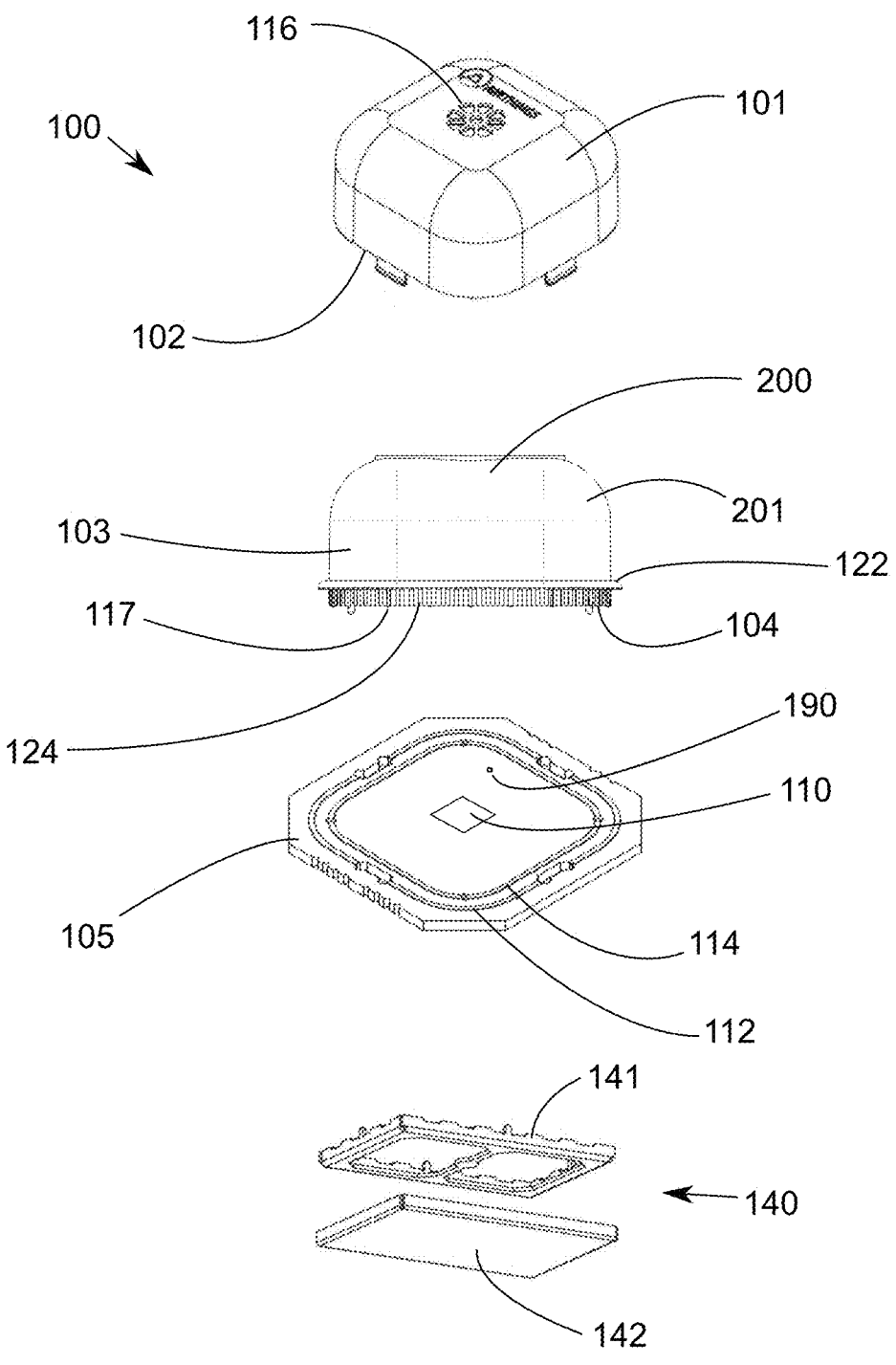
FIG. 1 shows an exploded view of various components of a radon gas sensor.

Various components of a radon gas sensor 100 according to an embodiment of the invention are shown in FIG. 1. These components are shown in an exploded configuration to show their order of assembly, although they are not all shown from the same perspective. These include, an outer dome 101, in inner dome 103, a printed circuit board 105 and a faraday cage 140.

The printed circuit board 105 has a photosensor 110 mounted on one side 111 and a hole 190 in its surface conductive layer 181 through which light can pass. The hole 190 is only in the surface conductive layer 181 and does not extend through the underlying substrate of the printed circuit board 105 so that it is impermeable to air.

The inner dome 103 is opaque to light and, when mounted on the printed circuit board 105 (specifically by mounting its rim 104 to the conductive trace 114 on the printed circuit board), it forms an opaque chamber. This opaque chamber forms the diffusion chamber of the radon gas sensor 100. Spacers 117 formed on the rim 104 of the inner dome 103 provide a small opening by which air can diffuse underneath the rim 104 and into the interior of the chamber which defines the sensitive volume for the radon gas sensor 100.

The outer dome 101 is mounted over the top of the inner dome 103 and serves as an electromagnetic shield which protects the inner dome 103 from electromagnetic interference as well as forming a diffusion path 115 between an opening 116 in the roof of the outer dome 101 and down between the two domes 101, 103 towards the rim 104 of the inner dome 103. Outer dome 101 is electrically connected to the printed circuit board 105 via its rim 102 contacting conductive trace 112. As can be seen in FIG. 2, a gasket 120 located between the inner dome 103 and the outer dome 101 is pressed against the printed circuit board 105 by a lip 122 formed on the outer surface of the inner dome 103. The diffusion path 115 passes over the top of the gasket 120 and down towards the rim 104 between the gasket 120 and the outer surface of the inner dome 103 via air channels 124 formed in the underside of the lip 122 and the outer surface of the inner dome 103. The gasket 120 seals against the printed circuit board, thereby preventing air and light from entering the inner dome 103 under its rim 104 and the gasket seals against the inner surface of the outer dome 101 thereby preventing air from entering the diffusion path other than at the opening 116 in the roof of the outer dome 101.

The photosensor 110 is the only electrical component mounted on the first side 111 of the printed circuit board 105 (mounted in a permanent conducting sense). The photosensor 110 is wire bonded to the printed circuit board 105 in a clean room environment so as to avoid unwanted contamination from soldering processes. On the other hand, other electrical components such as processing circuits 130 (indicated in FIG. 2) can be surface mounted on the second (opposite) side 118 of the printed circuit board 105 in a separate process.

A Faraday cage 140 is provided over at least some of the electrical components 130 on the second side 118 of the printed circuit board 105 to shield them from electromagnetic interference. The Faraday cage 140 shown here is a two part structure comprising a frame 141 which is soldered (surface mounted) onto the second side 118 of the printed circuit board 105 and a cover 142 which attaches to the frame in a separate assembly step. It will be appreciated that the Faraday cage 140 attaches to the underside 118 of the printed circuit board 105 in FIG. 1. When attached to the printed circuit board, the frame 141 is interposed between the cover 142 and the printed circuit board 105.

The assembled structure of the gas sensor 100 can be seen in cross-section in FIG. 2.

FIG. 2 illustrates in more detail the arrangement of the light source 150, the printed circuit board 105 and the photosensor 110.

The light source 150 in this embodiment is a reverse mount surface mount light emitting diode. Being a reverse mount component mean that when the component 150 is mounted to the printed circuit board 105, the light emitting structure 151 is arranged to point in towards the printed circuit board 105 rather than away from it as would be the case with a standard mount component. The light source 150 is shown in more detail in FIG. 4 which shows four views of the light source 150. The central view is towards the light emitting structure 151 and shows the central light emitting structure 151 with two electrodes 152 either side of it. The light emitting structure 151 and the two electrodes 152 are all on the same side of the component so that when the electrodes 152 are mounted to face the printed circuit board 105, the light emitting structure 151 also faces (and projects towards) the printed circuit board 105. The right view of FIG. 4 shows a side view of the light source 150 and shows how the light emitting structure 151 projects away from the back plate 153 of the component and therefore away from the electrodes 152. Accordingly, when the electrodes 152 are mounted against the second side 118 of the printed circuit board 105, the light emitting structure 151 needs to be accommodated in a recess 160 in the printed circuit board 105.

FIG. 2 shows the light source 150 installed in the recess 160 in the second side 118 of the printed circuit board 105. Importantly, it can be seen that the recess 160 is a blind hole, i.e. it does not extend all the way through the printed circuit board 105 from the second side 118 to the first side 111, but rather only extends part way through the printed circuit board 105. Thus the recess 160 is closed to the passage of air and is therefore impermeable to air. Therefore the recess 160 does not provide an alternative path for air to enter the chamber of the inner dome 103, leaving the air within the inner dome 103 defined by the characteristics of the diffusion path 115.

As the recess 160 is a blind hole, light from the light emitting structure 151 of the light source 150 is obstructed by the intact portion of the printed circuit board 105. However, as the printed circuit board 105 is made from a translucent material (typically a fibre-reinforced polymer of the FR4 type), the light is not completely obstructed, but a portion still passes through the printed circuit board 105 and into the opaque chamber formed by the inner dome 103.

FIG. 2 shows rays 170 of light emitted from the light source 150 and passing through the printed circuit board 105 into the interior of inner dome 103. The rays 170 strike the reflective inside of the inner dome 103. Some rays 171 are reflected or scattered towards the photosensor 110 while other rays 172 are reflected or scattered in different directions (the onward rays are not shown in FIG. 2 as they do not directly reach the photosensor 110, although it will be appreciated that they may still arrive there after multiple reflections/scatterings). The inside of the inner dome 103 may be reflective due to the material of the inner dome 103. For example it may be made from metal. Alternatively, it may be reflective due to a coating applied to the inner dome 103. For example the inner dome 103 may be formed from plastic which is then metalized to coat the plastic in a thin metal layer. In other embodiments a layer of scintillating material such as Silver-doped Zinc Sulphide may be provided in the interior of the dome 103 (or at least parts thereof), this material also being reflective. Scintillating material may be used for example where the photosensor 110 is a photomultiplier, e.g. in a radon gas sensor based on the principles of a lucas cell.

Figure 5:
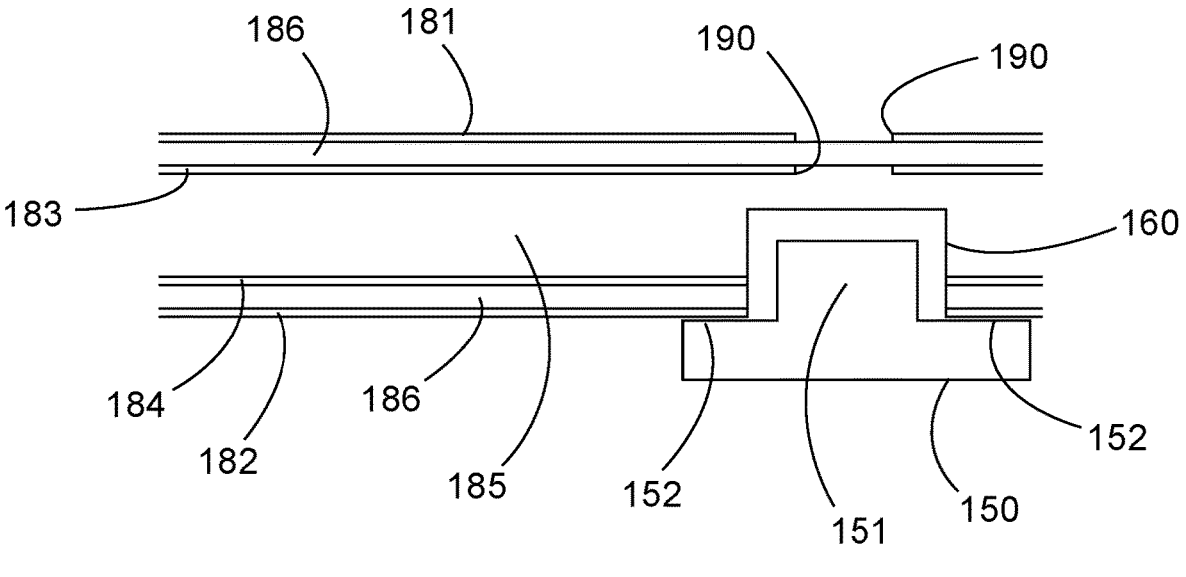
FIG. 5 shows a close up cross-section of a printed circuit board.

The recess 160 may be formed by drilling or milling part way through the printed circuit board 105. The printed circuit board 105 is a multilayer printed circuit board which in this embodiment has four conductive layers; two surface conductive layers 181, 182 (one on the first side 111 and one on the second side 118) and two intermediate layers 183, 184 as shown in FIG. 5. The four conductive layers 181, 182, 183, 184 are opaque to light. The two intermediate layers 183, 184 are separated by a core substrate layer 185 which is FR4 glass-fibre reinforced polymer and is translucent. The two surface layers 181, 182 are separated from the respective intermediate layers 183, 184 by a prepreg layer 186 of glass-fibre reinforced polymer which is translucent. The recess 160 has been drilled from the second side 118 just over half way through the core substrate layer 185, but not all the way through, i.e. the recess 160 is a blind hole. The drilling process has formed holes in the conductive layers 182, 184 and the intervening prepreg layer 186, so light from the light source 150 is unobstructed by these layers. However, the recess 160 does not affect the conductive layers 181, 183 and therefore to ensure that these do not obstruct light from being transmitted from the light source 150 and out through the first side 111 of the printed circuit board 105, the surface conductive layer 181 and the intermediate conductive layer 183 have been etched in the region lying above the recess 160. In this example the size of the etched holes 190 is smaller than the size of the recess 160, but that need not be the case. However, in this embodiment the size of the etched hole 190 in the surface conductive layer 181 on the first side 111 of the printed circuit board 105 defines the exit aperture for the light from the light source 150. Together, the geometry of this hole and the position of the light source 150 determine the size and orientation of the cone of light that is projected into the inner dome 103.

In this embodiment, the etched holes 190 are directly above the recess 160 and the light source 150 so that the light is directed upwards around the normal to the printed circuit board 105. However, in other embodiments the etched holes 190 could be located more to one side to angle the light path into the inner dome 103.

The etched holes 190 are small in area, in this embodiment being circular holes about 1 mm in diameter. The rest of the surface conductive layer 181 is substantially continuous in the region around the etched hole 190. This is because it is used to from the electric field that drives charged radon daughter products towards the photosensor 110. It is desirable for this electric field to be as uniform and strong as possible and therefore it is desirable to make the etched hole 190 (and other breaks in the conductive layer 181 within the inner dome 103) as small as possible. Another break is required around the photosensor 110 itself as the photosensor 110 is held at a different potential, but the conductive layer 181 can be otherwise substantially continuous.

The same applies to the intermediate conductive layer 183 as this layer is used as part of a Faraday shield together with the outer dome 101 that completely surrounds the inner dome 103, thereby protecting it from electromagnetic interference. Accordingly, the etched hole 190 in the intermediate conductive layer 183 is as small as possible, while the remainder of the intermediate conductive layer 183 is substantially uninterrupted (apart from necessary breaks to allow electrical connection to the surface conductive layer 181 and inner dome 103 and the photosensor 110).

As can be seen in FIGS. 1, 2 and 3, the light source 150 and corresponding recess 160 and etched holes 190 are located at a distance from the photosensor 110 so that the effect of the etched holes 190 on the electric field is minimal and is far away from the photosensor 110 (it is closer to the wall of the inner dome 103). In FIG. 3 it can also be seen that the conductive trace 114 to which the rim 104 of the inner dome 103 is electrically connected is a continuous area of the first surface conductive layer 181 which surrounds the photodiode 110 and which acts, together with the inner dome 103 (which is also conductive) to form a Faraday cage around the photosensor 110 and also a high voltage anode for creating an electric field with the negatively biased photosensor 110.

In this embodiment, there is a further advantage of this positioning of the light source 150 which is due to the shape of the inner dome 103. As can be seen in FIG. 1, the inner dome (and the outer dome 101 which is the same shape as the inner dome 103 but slightly larger) is a rounded cuboid shape, i.e. a cuboid shape with a roof and perpendicular walls, but with rounded edges 200 and rounded corners 201 connecting the roof to the walls and the walls to each other. When light from the light source 150 is directed at one of the rounded edges 200 or rounded corners 201, the light is reflected (redirected) across a wide range of angles within the inner dome 103 which spreads across the photosensor 110. Light from the light source 150 that is directed at a rounded corner (doubly-curved) rather than a rounded edge (singly-curved) is conveniently spread in this manner in two dimensions.

It will be appreciated that the geometry of the opaque chamber could be other than that shown in the figures. For example it could be a hemispherical dome or a cylindrical dome. It could be a rectangular or cylindrical shape with sharp corners or with rounded edges/corners of larger or smaller radius or indeed a number of other shapes. The positioning and directing of the light source 150 can be determined appropriately according to the particular geometry of the chamber and the relative position of the photosensor 110.

It will be appreciated that many variations of the above embodiments may be made without departing from the scope of the invention which is defined by the appended claims.

The invention claimed is:

1. A radon gas sensor comprising:
a printed circuit board;
a photosensor mounted on a first side of the printed circuit board;
a light source mounted on a second, opposite side of the printed circuit board; and
an opaque diffusion chamber mounted on the first side of the printed circuit board over the photosensor
wherein the light source is arranged to transmit light through at least a portion of the printed circuit board, said portion being impermeable to air; and
wherein the light source is arranged such that the light transmitted through the printed circuit board is transmitted into the inside of the opaque diffusion chamber.

2. A sensor as claimed in claim 1, wherein a blind hole is formed in the second side of the printed circuit board and wherein the light source is arranged to transmit light into the blind hole.

3. A sensor as claimed in claim 2, wherein the blind hole has a depth equal to at least a quarter the thickness of the printed circuit board, preferably at least a third the thickness of the printed circuit board, preferably at least half the thickness of the printed circuit board.

4. A sensor as claimed in claim 2, wherein the light source is at least partially located within the blind hole.

5. A sensor as claimed in claim 1, wherein the printed circuit board comprises a substrate layer of translucent electrically insulating material.

6. A sensor as claimed in claim 1, wherein the first side of the printed circuit board comprises a first opaque conductive layer on the surface of the first side opposite the light source and wherein the first opaque conductive layer comprises a hole to allow light from the light source to pass through.

7. A sensor as claimed in claim 6, wherein the hole in the first opaque conductive layer is no more than 5 mm wide in any dimension.

8. A sensor as claimed in claim 1, wherein the printed circuit board further comprises a second opaque conductive layer located within the printed circuit board and wherein the second opaque conductive layer comprises a hole to allow light from the light source to pass through.

9. A sensor as claimed in claim 8, wherein the hole in the second opaque conductive layer is no more than 5 mm wide in any dimension.

10. A sensor as claimed in claim 8, wherein the first opaque conductive layer and the second opaque conductive layer are separated by a layer of translucent electrically insulating material.

11. A sensor as claimed in claim 1, wherein the light source is a reverse assembly surface mount light source.

12. A sensor as claimed in claim 1, wherein the light source is a light emitting diode.

13. A sensor as claimed in claim 1, wherein the light source is located within an opaque enclosure mounted on the second side of the printed circuit board.

14. A sensor as claimed in claim 1, wherein an inside surface of the opaque chamber is reflective.

15. A sensor as claimed in claim 1, herein an inside surface of the opaque chamber is partially covered with a scintillating material.

16. A sensor as claimed in claim 1, wherein the inside surface of the opaque chamber has a doubly-curved region and wherein the light source is arranged to transmit light towards the doubly-curved region.

17. A sensor as claimed in claim 1, wherein the photosensor comprises a photodiode and/or a semiconductor photomultiplier.

18. A method of testing a radon gas sensor comprising a photosensor mounted on a first side of a printed circuit board and an opaque diffusion chamber mounted on the first side of the printed circuit board over the photosensor, the method comprising:
transmitting light into the inside of the opaque diffusion chamber from a light source mounted on a second side of the printed circuit board through at least a portion of the printed circuit board, said portion being impermeable to air; and
receiving said light at said photosensor.

* * * * *